(12) United States Patent
Chau et al.

(10) Patent No.: US 9,086,346 B2
(45) Date of Patent: Jul. 21, 2015

(54) METHOD FOR PROCESSING A SENSOR CHIP

(75) Inventors: Lai-Kwan Chau, Chiayi County (TW); Guo-Hua Feng, Chiayi County (TW); Wei-Ting Hsu, Chiayi County (TW); Cheng-Lung Cho, Chiayi County (TW)

(73) Assignee: National Chung Cheng University, Minhsiung Township (TW)

( * ) Notice: Subject to any disclaimer, the term of this patent is extended or adjusted under 35 U.S.C. 154(b) by 943 days.

(21) Appl. No.: 13/278,230

(22) Filed: Oct. 21, 2011

(65) Prior Publication Data

US 2013/0102089 A1 Apr. 25, 2013

(51) Int. Cl.
| | |
|---|---|
| *G01N 1/00* | (2006.01) |
| *G01N 1/40* | (2006.01) |
| *B82Y 15/00* | (2011.01) |
| *G01N 1/28* | (2006.01) |

(52) U.S. Cl.
CPC ............... *G01N 1/405* (2013.01); *B82Y 15/00* (2013.01); *G01N 1/286* (2013.01); *Y10T 436/25* (2015.01); *Y10T 436/25125* (2015.01)

(58) Field of Classification Search
CPC ......... G01N 1/405; G01N 1/286; B82Y 15/00
See application file for complete search history.

(56) References Cited

U.S. PATENT DOCUMENTS 5,834,871 A * 11/1998 Puskas ..................... 310/316.02

OTHER PUBLICATIONS

Disley, Darren M. et al. "Covalent coupling of immunoglobulin G to self-assembled monolayers as a method for immobilizing the interfacial-recognition layer of a surface plasmon resonance immuniosensor." Biosensor & Bioelectronics (1998) 13 1213-1225.*
Cullar, Stefan et al. "Removal of nonspecifically bound proteins on microarrays using surface acoustic waves." IEEE Sensors Journal (2008) 8 314-320.*
Wei-Sing Chu, et al., "Ultrasound-accelerated formalin fixation of tissue improves morphology, antigen and mRNA preservation", Modern Pathology (2005) 18: 850-863.
Richard W. Ellis, et al., "Diagnostic particle agglutination using ultrasound: a new technology to rejuvenate old microbiological methods", J. Med. Microbiol (2000) vol. 49, 853-859.

* cited by examiner

*Primary Examiner* — Christopher A Hixson
(74) *Attorney, Agent, or Firm* — Fishman & Associates, LLC.

(57) ABSTRACT

The method for processing a sensor chip in accordance with the present invention has: 1) providing an acoustic wave operation system and a biochemical sensor chip, wherein the acoustic wave operation system has a piezoelectric transducer generating at least one cycle of longitudinal acoustic waves by a driving voltage and wherein a probe is immobilized on a surface of the biochemical sensor chip; 2) arranging the piezoelectric transducer at a distance from the biochemical sensor chip and filling therebetween with a medium for transmitting longitudinal acoustic waves; and 3) applying longitudinal acoustic waves to the biochemical sensor chip to remove an adsorbate bound to the probe.

10 Claims, 10 Drawing Sheets

METHOD FOR PROCESSING A SENSOR CHIP

BACKGROUND OF THE INVENTION

1. Field of the Invention

The present invention relates to a method for processing a sensor chip, especially to a method for processing a chip for biological or chemical use wherein longitudinal acoustic waves are employed to remove non-specifically bound adsorbates or interfering adsorbates, as well as to regenerate sites for specifically bound adsorbates or target adsorbates.

2. Description of the Prior Art

Over the past few decades a large increase of research literature about the application of ultrasonic energy can be found in different scientific fields, especially for chemistry and biology. In general, the prior art has indicated that ultrasound facilitates chemical analyses. For example, ultrasound is considered capable of speeding up enzymatic reactions, accelerating measurements by enhancing mass transport, enhancing solid-liquid elemental extraction, as well as using cavitation effects for causing the formation and collapse of liquid micro jet to induce a rapid stirring of the liquid. See: *Ultrasound in Chemistry: Analytical Applications* (ISBN: 978-3-527-31934-3), *Modern Pathology* (2005) 18:950-863, and *J. Med. Microbiol.* (2000) 49:853-859. Other than the aforementioned applications, utilizing ultrasonic waves to manipulate biomolecule specifically further enables numerous potential applications. For instances, it enhances the sensing sensitivity and improves signal-to-noise ratio as described in *Int. J. Legal Med* (2009) 123:521-525, mixes or separates the particles in microfluidic regime with fast response time as described in *Chemical Society Reviews* (2007) 36:492-506 and *Sensors and Actuators B* (2003) 95:425-434, lyses the cells to obtain proteins and DNA as described in *Biophysics* (2008) 53(3): 250-251 or deposits cells onto the desired location in a biochip as described in *Biosensors and Bioelectronics* (2004) 19:1021-1028.

As described in *Sensors and Actuators B* (2007) 121:452-461, it is beneficial to use ultrasonic forces to manipulate bioparticles. Under activation of ultrasonic waves, a force field is generated by the vibrating source that couples the pressure transmitted through a fluidic medium. The force field manipulates biomolecules with a pressure exerted on the whole surfaces of these molecules. Thus, various functions would be achieved. For example, more kinetic energy can be provided to enhance specific molecular binding or to reduce aggregation of non-specific particles. The interaction of reactant and reagent can be more efficient than a diffusion-based reaction. Additionally, compared with other methods for manipulating bioparticles, ultrasound surpasses dielectrophoresis because the electrical properties of the biomolecules and the fluid medium employed are not of major concern. The direct contact force applied by an instrument, for example, a solid tip, may damage the bioparticles. Non-contact force induced by ultrasound is free from the aforementioned damage done by direct contact.

In terms of bioassay usage, non-specific molecular binding can lower the sensitivity of bio-detection because noise suppresses signals. This could be a serious problem and thus removing non-specific molecules that bind to or aggregate at specific detection regions allows effective target-probe interactions and increases the detectable signals from the bindings of target adsorbates and probes. Therefore, sensing enhancement can be achieved by improving the sensitivity, lowering the detection limit, and even reducing the sensing time.

In addition, to regenerate the activity of the immobilized sensing probes after reacting with target adsorbates, or analytes, and then breaking the linkage thereof for repeat usage is also important for biochemical detection. This would be more valuable when dealing with some expensive or rare molecules. Fast and reliable regeneration process could also shorten the time necessary for preparing immobilized probe molecules onto the biosensor substrates, and lessen the adverse effect to the environment due to massive biochips with only one-time usage capability.

To overcome the shortcomings, the present invention provides a method for processing a sensor chip to mitigate or obviate the aforementioned problems.

SUMMARY OF THE INVENTION

The main objective of the invention is to provide a method for processing a sensor chip.

The method for processing a sensor chip in accordance with the present invention has:

providing an acoustic wave operation system and a biochemical sensor chip, wherein the acoustic wave operation system has a piezoelectric transducer generating at least one cycle of longitudinal acoustic waves by a driving voltage and wherein a probe is immobilized on a surface of the biochemical sensor chip;

arranging the piezoelectric transducer at a distance from the biochemical sensor chip and filling therebetween with a medium for transmitting longitudinal acoustic waves; and applying longitudinal acoustic waves to the biochemical sensor chip to remove an adsorbate bound to the probe.

Preferably, the frequency range of the longitudinal acoustic waves is from 100 kHz to 1 MHz.

Preferably, a cycle of longitudinal acoustic waves comprises longitudinal acoustic waves of a swept-frequency sweeping from 100 kHz to 1 MHz and then back to 100 kHz in a period of time.

Preferably, the piezoelectric transducer applies multiple cycles of longitudinal acoustic waves to the biochemical sensor chip.

Preferably, the biochemical sensor chip further comprises a noble metal nanoparticle layer formed on the surface of the biochemical sensor chip and the probe is attached to the noble metal nanoparticle layer.

Preferably, the medium is selected from the group consisting of: aqueous buffer solution and water.

Preferably, a driving voltage ranging from 0 $V_{rms}$ to 200 $V_{rms}$ is applied to the piezoelectric transducer for removing adsorbates non-specifically bound to the probe or adsorbates specifically bound to the probe.

Preferably, the driving voltage applied to the piezoelectric transducer is larger than 10 $V_{rms}$ for removing interfering substances non-specifically bound to the probe.

Preferably, the driving voltage applied to the piezoelectric transducer is larger than 10 $V_{rms}$ for removing adsorbates specifically bound to the probe.

Though the volume of the acoustic waves, which is relevant to the amplitude of the driving voltage, may possibly be one of the factors for removing non-specific or specific binding, research findings to date have demonstrated that the frequency change of the driving voltage is also a factor thereof. A forcible definition based on volume of the acoustic waves is practically inconvenient.

Preferably, the probe is selected from a group consisting of: antibody, antigen, lectin, hormone receptor, peptide, nucleic acid, aptamer, oligosaccharide, cell receptor, chemical recognizing molecule, and a corresponding analyte capable of specifically binding to the probe as a target.

Preferably, the biochemical sensor chip is selected from a group consisting of: particle plasmon resonance (PPR) sensor, surface plasmon resonance (SPR) sensor, quartz crystal microbalance, and fluorescence sensor chip.

Preferably, the acoustic wave operation system further has a waveform generator and a signal amplifier. The waveform generator is for generating a load signal, wherein the load signal is amplified by the signal amplifier and transmitted to the piezoelectric transducer for further transmitting.

The method in accordance with the present invention provides at least the following advantages:

1) With the acoustic wave operation system a longitudinal acoustic wave is applied to the biochemical sensor chip for removing interfering biochemical molecules non-specifically bound to the probe so as to raise the sensitivity of the biochemical sensor chip. The longitudinal acoustic wave may also be applied to the biochemical sensor chip for removing target adsorbates, or analytes, specifically bound to the probe so as to regenerate the biochemical sensor chip, allowing repetitive use of the biochemical sensor chip, which is economical and cost-effective.

2) The biochemical sensor chip is modified with noble metal nanoparticles, to which the probe is linked, that are highly stable under activation of longitudinal acoustic waves, and thus is suitable for effective regeneration.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
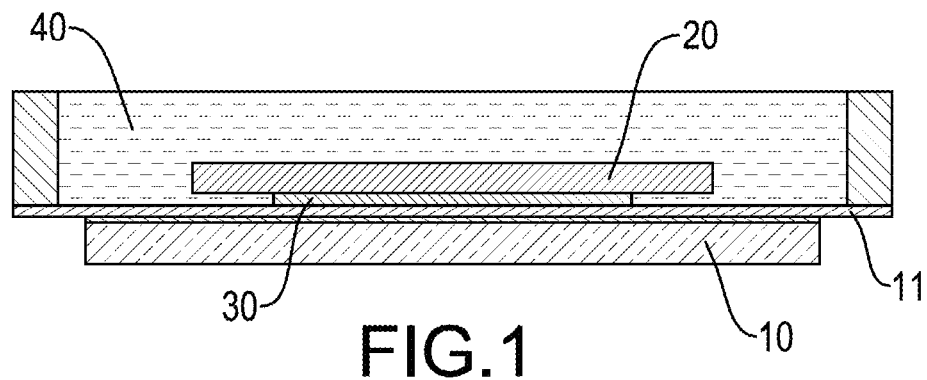
FIG. 1 is a cross-sectional side view of an acoustic wave operation system in accordance with the present invention.

A process for constructing and examining an acoustic wave operation system in accordance with the present invention primarily comprises the following steps 1), 2) and 3):

1) Applying a monolayer of Au nanoparticles onto a GSC and attaching biotin to the monolayer of Au nanoparticles to obtain a prepared biochemical sensor chip. The biotin is used as a probe immobilized on the surface of the biochemical sensor chip. A target adsorbate corresponding to the probe may be biotin, streptavidin, anti-biotin antibody, anti-fibrinogen antibody, and bovine serum albumin (BSA). The biochemical sensor chip is submerged in a predefined amount of buffer solution received in a micro chamber of a prepared acoustic wave operation system.

2) Employing a piezoelectric transducer as a source of longitudinal acoustic waves. The piezoelectric transducer is attached to a bottom of the chamber and a varying electric field with frequency-sweep function is applied to an actuator element of the piezoelectric transducer to generate longitudinal acoustic waves toward the biochemical sensor chip, so as to obtain a longitudinal-acoustic-wave-processed biochemical sensor chip.

3) Using ultraviolet-visible spectroscopy to analyze the number of the target adsorbate molecules specifically bound to the probe immobilized on the surface of the biochemical sensor chip.

The methods, materials and results of the aforementioned process for constructing and examining an acoustic wave operation system in accordance with the present invention is further described in the following examples. It is to be noted that these illustrative examples are for exemplifying or illustrating the characteristics of the present invention without any intention to limit the scope of the present invention in any aspect.

Example 1

The instant example exemplifies materials used for following examples or feasible practices of the present invention.

1) Materials and Instruments

GSC with dimensions of a length of 76.2 mm, a width of 25.4 mm and a thickness of 1.0 mm, purchased from Shan-chun business.

Thermometer, Model-304, Center technology Corp model.
Spectrophotometer, V-570, Jusco.
Transmission electron microscope, Model-2010 EX, Joel.

2) Reagents

The following chemicals are commercially available and were used as received. All aqueous solutions were prepared with water that had been purified with a Millipore Milli-Q water purification (Millipore) at a specific resistance of 18.2 MΩ-cm.

n-hexadecyltrimethylammonium bromide (CTAB, Fluka).
sodium borohydride (Lancaster)
3-(mercaptopropyl)-trimethoxysilane (MPTMS, Acros)
2-(4-(2-hydroxyethyl)-1-piperazinyl)-ethanesulfonic acid (HEPES, Fluka)
1-ethyl-3-(3-dimethylaminopropyl)-carbodiimine hydrochloride (EDC, Fluka)
biotin (Aldrich)
streptavidin (Fluka)
anti-fibrinogen antibody (Sigma)
anti-biotin antibody (Sigma)
BSA (Sigma)

Example 2

The instant example demonstrates the preparation of Au nanoparticles.

1.78 mL of 25.4 mM aqueous solution of hydrogen tetrachloroaurate, 8.22 mL of chloroform, and 0.4 mL of a 0.02 M ethanol solution of CTAB were mixed and stirred for 10 minutes to form a $4.52 \times 10^{-4}$ M hydrogen tetrachloroaurate solution. 0.8 mL of freshly prepared 0.15 M $NaBH_4$ ethanol solution was added to the aforementioned hydrogen tetrachloroaurate solution with vigorous stirring. After the solution was further stirred for 30 minutes, a ruby-colored organic phase was separated. Absorbance spectra of the samples were obtained by using a spectrophotometer. In the instant example, a Jusco V-570 spectrophotometer was used. Transmission electron microscopic (TEM) observations of the samples, which had been dispersed and allowed to dry on copper grids, were taken with a Joel TEM 2010 EX instrument. Histograms derived from TEM image analysis showed that the mean diameter of the Au colloids was 15.9±2.5 nm.

Example 3

The instant example demonstrates the preparation of Au nanoparticle-modified GSC.

In the instant example, a GSC was cut by a diamond glass cutter to a dimension of a length of 14.0 mm, a width of 9.0 mm and a thickness of 1.0 mm. The cut GSC was cleaned for 30 minutes in a bath consisting of 3 volumes of 30% $H_2O_2$ and 7 volumes of concentrated $H_2SO_4$.

The cleaned GSC was then submerged into vials containing 1% solution of MPTMS in toluene. After 12 hours, the GSC was rinsed with methanol and putted into an oven at 60° C. for 30 minutes to remove unbound monomers from the surface to obtain a pretreated GSC.

After the pretreatment including the aforementioned rinsing and drying procedures, the GSC was immersed in an Au nanoparticles solution with absorbance of about one at a wavelength of 523 nm for 12 hours to obtain a GSC with an Au nanoparticle layer being a monolayer of self-assembled Au nanoparticle. The GSC modified with the monolayer of Au nanoparticle (hereinafter "PPR-GSC") was subsequently rinsed sequentially with water, methanol, and chloroform.

Example 4

The instant example demonstrates the immobilization of biotin onto the PPR-GSC.

The processed PPR-GSC was modified by a self-assembled monolayer (SAM) of cystamine. This is performed by immersing the PPR-GSC into a cystamine dihydrochloride solution at room temperature for 2 hours. The cystamine-modified PPR-GSC was further functionalized with biotin by immersion of a solution of HEPES, EDC, and biotin at room temperature for 2 hours, and was then rinsed with water and air-dried at room temperature. For subsequent nonspecific binding removal and regeneration, the biotin-functionalized PPR-GSC was immersed into a solution of PBS buffer solution containing a target adsorbate, for example, anti-biotin antibody, streptavidin, or anti-fibrinogen antibody, at room temperature for 2 hours, which was later rinsed with water and air-dried at room temperature.

Example 5

The instant example demonstrates the measuring of elimination of non-specific binding and regeneration of specific binding sites.

With reference to FIG. 1, the acoustic wave operation system comprises a waveform generator (Model AFG-3021, Tektronix Instrument Co.), a signal amplifier (Model 325LA, EIN Instrument Co.), a piezoelectric transducer 10 made of lead zirconate titanate (PZT), an operation chamber having a flat base 11 made of glass, a biotin-functionalized PPR-GSC 20, and two gaskets 30 made of polydimethylsiloxane (PDMS).

The gaskets 30 were placed on the base 11 of the operation chamber and the biotin-functionalized PPR-GSC 20 was placed on the two gaskets 30, so as to allow the gaskets 30 to serve as spacers to maintain a constant distance between the base 11 of the operation chamber and the PPR-GSC 20. Preferably, two edge portions of the PPR-GSC 20 are placed onto the gaskets 30.

Longitudinal acoustic waves were generated from sinusoidal signals transmitted by the piezoelectric transducer 10, wherein the sinusoidal signals were generated by the waveform generator and amplified by the signal amplifier before transmission to the piezoelectric transducer 10. The sinusoidal signals generated by the waveform were of a swept-frequency sweeping from 100 kHz to 1 MHz and then back to 100 kHz.

An amount of buffer solution 40 sufficient for fully covering the PPR-GSC was filled, by means such as pipetting, into the operation chamber. The buffer solution 40 served as a medium for transmitting longitudinal acoustic waves. At actuation or activation of the piezoelectric transducer 10 driven with the amplified sinusoidal signals, the piezoelectric transducer 10 propagated longitudinal acoustic waves to the biotin-functionalized PPR-GSC towards the PPR-GSC 20.

The acoustic wave operation system was applied in the instant example to investigate two effects about biosensing: 1) elimination of non-specific binding and 2) regeneration of specific binding sites. Biotin was immobilized on the PPR-GSC 20 and, as set forth in the foregoing example, attached to the Au nanoparticles coated on the surface of the PPR-GSC 20, served as a probe for the investigations of both effects. Anti-fibrinogen antibody or BSA was selected as an interfering adsorbate to examine their interactions with biotin. Anti-biotin antibody or streptavidin was chosen as a target adsorbate bound onto the probe. The target-probe interactions were confirmed by UV-visible spectroscopy. Absorbance spectra of the aforementioned Au nanoparticles coated on the biotin-functionalized PPR-GSC 20 were taken by a UV-vis spectrophotometer (Model V-570, Jusco).

Example 6

The instant example demonstrates the mechanism of the biotin-functionalized PPR-GSC.

Figure 2:
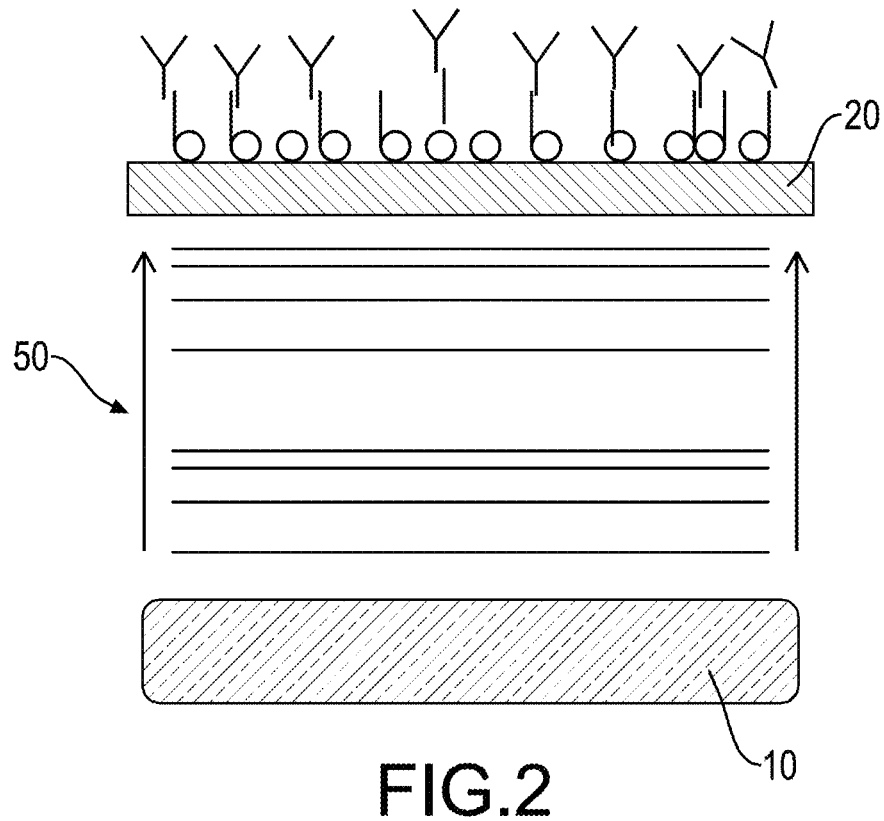
FIG. 2 is a schematic graph of a piezoelectric transducer in accordance with the present invention transmitting longitudinal acoustic waves to the biotin-functionalized particle plasmon resonance-glass slide chip (hereinafter "PPR-GSC")
Figure 3:
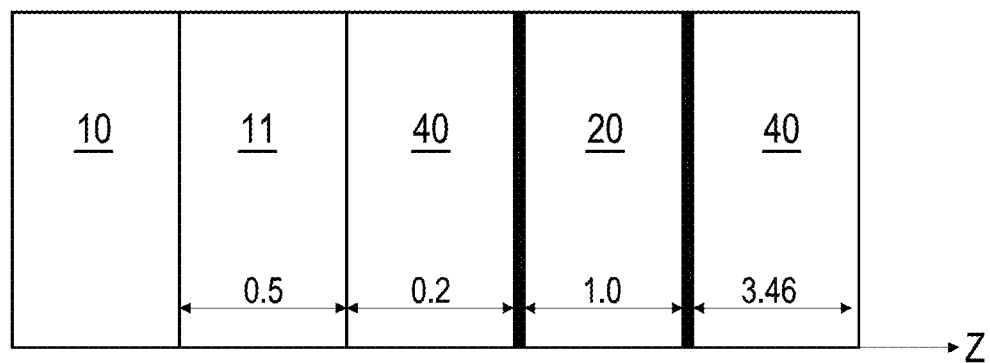
FIG. 3 is a schematic graph of a path along which longitudinal acoustic waves in accordance with the present invention are transmitted.

With reference to FIG. 2, the biotin-functionalized PPR-GSC 20 was arranged at a suitable distance from and parallel to the piezoelectric transducer 10. Specifically, the distance between the PPR-GSC 20 and the piezoelectric transducer 10 was around wavelength range of the longitudinal acoustic waves 50. With further reference to FIG. 3, the longitudinal acoustic waves 50 generated from the piezoelectric transducer 10 could thus be considered as plane wave propagated in the direction perpendicular to the piezoelectric transducer 10 and the PPR-GSC 20, that is, traveling along the z-axis.

In the instant example, specifically, the piezoelectric transducer 10 was glued onto the base 11 of a thickness of 0.5 mm. The PPR-GSC 20 was of a thickness of 1.0 mm and was double-side coated with Au nanoparticles. The PPR-GSC 20 was 0.2 mm away from the base 11. PBS was used in the instant example as the buffer solution 40 serving as the medium to couple the longitudinal acoustic waves 50 from the piezoelectric transducer 10 to the Au nanoparticle layer coated on the PPR-GSC 20.

When the piezoelectric transducer was activated, longitudinal acoustic waves 50 were transmitted along a straight forward path for the generated longitudinal acoustic waves 50 to pass through the 0.5 mm thick PPR-GSC 20 and a 0.2 mm thick layer of the buffer solution 40 to exert acoustic forces on two opposite surfaces of the PPR-GSC 20 sequentially, that is, a first surface facing the gaskets 30 and the base 11 and then a second surface opposite to the first surface. The longitudinal acoustic waves 50 kept being transmitted through the buffer solution 40 to an interface of the buffer solution 40 and the air.

However, different acoustic impedances of various materials mismatch, as observed during longitudinal acoustic wave transmission. Due to the acoustic impedance that attenuates the energy of the longitudinal acoustic waves, the longitudinal acoustic waves could travel along a path of a limited distance in the materials and would thus be reflected. Therefore, only possible acoustic wave transmission paths, along which the transmission coefficient (as defined in Formula 1 below) from the source of longitudinal acoustic waves, or the piezoelectric transducer 10 set forth in the instant example, to the surfaces of the PPR-GSC is no less than 1% of the acoustic intensity of the source of longitudinal acoustic waves, were considered in the instant example.

Figure 4:
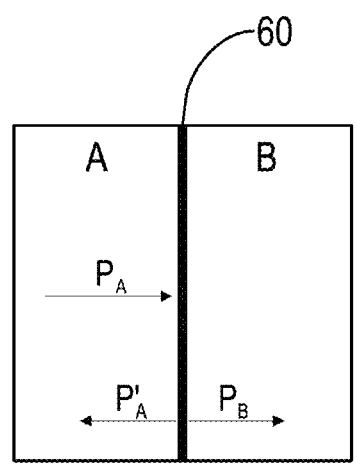
FIG. 4 is a schematic graph of reflected waves and penetrating waves as well as longitudinal acoustic waves from which the former two are generated.

As shown in FIG. 4, the acoustic intensity (I), transmission coefficient ($T_I$) and the reflection coefficient ($R_I$) of a longitudinal acoustic wave are defined in the following Formulae 1 and 2:

$$T_I = \frac{I_B}{I_A} = \frac{4(Z_A/Z_B)}{(1+Z_A/Z_B)^2}$$ (Formula 1)

$$R_I = \frac{I'_A}{I_A} = \left(\frac{1-Z_A/Z_B}{1+Z_A/Z_B}\right)^2$$ (Formula 2)

$I_A$ represents the acoustic intensity of an incident longitudinal acoustic wave $P_A$ to a flat object 60, $I'_A$ represents the acoustic intensity of a reflected wave $P'_A$, $I_B$ represents the acoustic intensity of a penetrating wave $P_B$ of the longitudinal acoustic wave $P_A$, and Z, as defined in the following Formula 3, represents the impedance of the object 60 against the longitudinal acoustic wave $P_A$, wherein $\rho$ is density of the object 60 and c is sound speed of the object 60. In the instant example, the impedances of the piezoelectric transducer, the PPR-GSC and the buffer solution are respectively, $3.04 \times 10^7$, $8.76 \times 10^6$ and $1.5 \times 10^6$ kg/m$^2$s.

$$Z = \rho \cdot c$$ (Formula 3)

Figure 5:
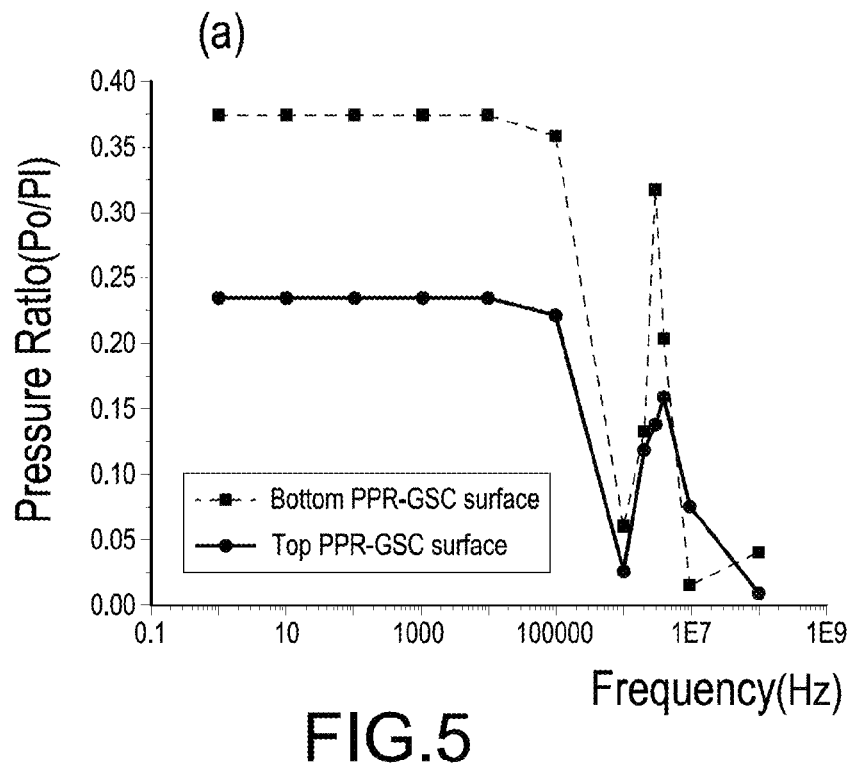
FIG. 5 is a line chart of the ratio of acoustic intensities exerting on gold nanoparticles (hereinafter "Au nanoparticles") coated on opposite surfaces (the first and second surfaces) of the biotin-functionalized PPR-GSC versus frequency.

With reference to FIG. 5, as set forth with the foregoing formulae, the ratio of acoustic intensities exerting on Au nanoparticles coated on opposite surfaces, that is, the first and second surfaces, of the biotin-functionalized PPR-GSC versus frequency changes when longitudinal acoustic waves of different frequencies are applied. As a result, a significant change of the ratio of acoustic intensities was observed within a predefined longitudinal acoustic frequency range, as exemplified in the instant example, from 100 kHz to 1 MHz.

Figure 6:
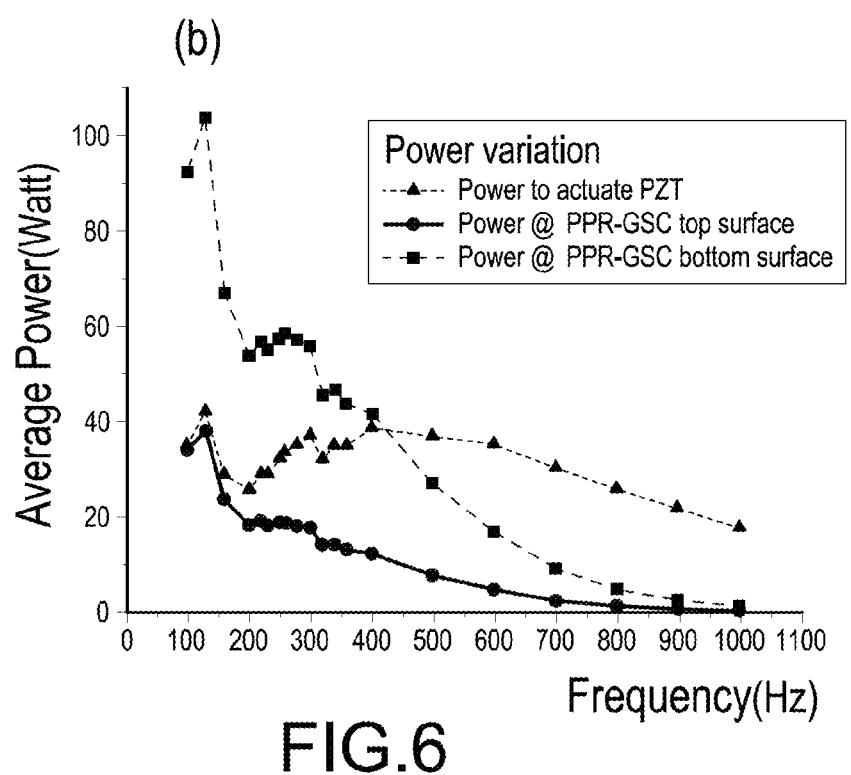
FIG. 6 is a line chart of the power acting on the Au nanoparticles coated on the opposite surfaces of the biotin-functionalized PPR-GSC versus frequency.

With further reference to FIGS. 3, 5 and 6, according to the readings of the signal amplifier, the acoustic intensities of the longitudinal acoustic waves were recorded, from which the changes of acoustic intensities on the Au nanoparticles coated on the opposite surfaces (the first and second surfaces) of the PPR-GSC 20 were calculated.

Example 7

The instant example demonstrates that the removal of non-specifically bound adsorbates and the regeneration of binding sites of specifically bound adsorbates are not due to temperature but longitudinal acoustic waves.

Figure 7:
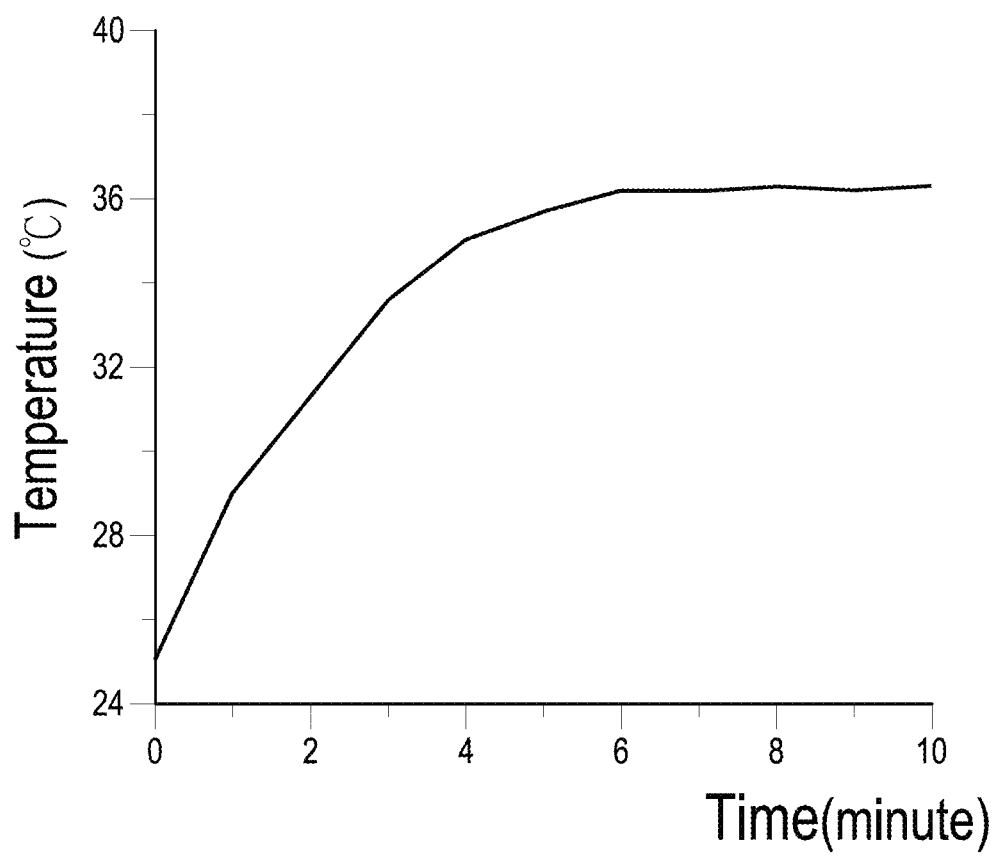
FIG. 7 is a line chart of temperature change along time under activation of longitudinal acoustic waves.

With reference to FIG. 7, that the longitudinal acoustic wave is the dominant factor and rules out the temperature effect was verified with a method comprising the following steps:

1) 1 mL of buffer solution was injected into the operation chamber.

2) The change of the temperature of the chamber was measured with a thermometer or a thermocouple.

As a result, in the initial stage of the operation of the acoustic wave operation system, the temperature of the buffer solution in the operation chamber was room temperature. Once the acoustic source, that is, the piezoelectric transducer, was activated, the temperature of the buffer solution gradually increased and reached a balance of 36° C. after 5 minutes. A temperature of 36° C. is not typically expected to practice the removal of non-specifically bound adsorbates, which may be biomolecules, and the regeneration of binding sites of specifically bound adsorbates, which may be biomolecules. Hence, the acoustic wave operation system functions due to the longitudinal acoustic waves generated by the piezoelectric transducer instead of due to the elevated temperature.

Example 8

The instant example demonstrates the stability of the Au nanoparticles coated on the PPR-GSC under longitudinal acoustic wave activation.

Figure 8:
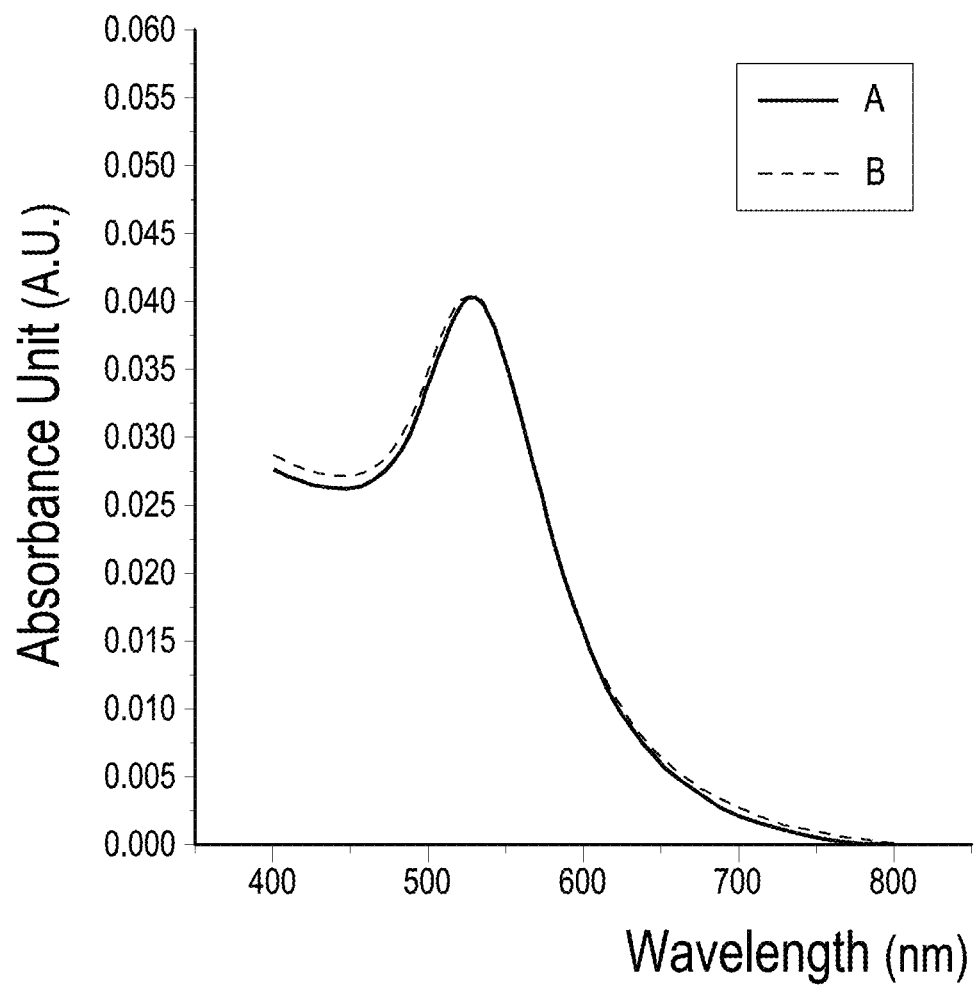
FIG. 8 is a line chart of absorbance spectra of the Au nanoparticles coated on the surface of biotin-functionalized PPR-GSC without or with being activated by longitudinal acoustic waves.
Figure 9:
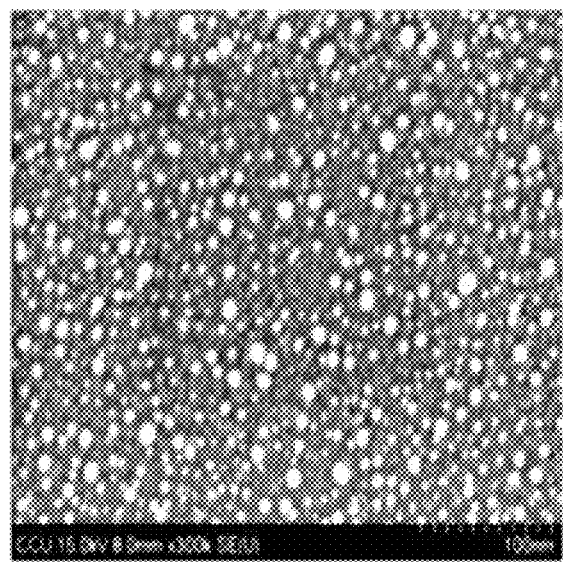
FIG. 9 is a field-emission scanning electron microscope (FE-SEM) image of the Au nanoparticles coated on biotin-functionalized PPR-GSC without being activated by longitudinal acoustic waves.
Figure 10:
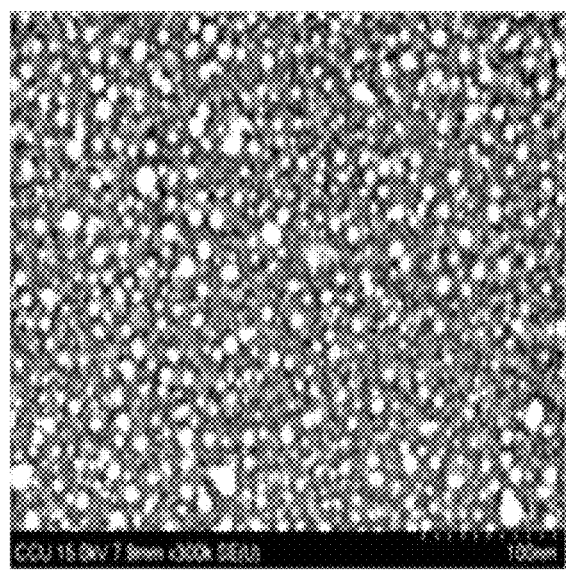
FIG. 10 is an FE-SEM image of the Au nanoparticles coated on biotin-functionalized PPR-GSC activated by longitudinal acoustic waves.

With reference to FIGS. 8 to 10, UV-visible spectrophotometry and FE-SEM were used to confirm the stability of Au nanoparticles coated on PPR-GSC under activation of the acoustic source, that is, the piezoelectric transducer. FIG. 5 shows the absorbance spectra of the PPR-GSC being activated (dotted line B) and without being activated (solid line A) by longitudinal acoustic waves. The two absorbance spectra represented as lines A and B in FIG. 8 highly overlap each other around the absorbance peak. The densities of Au-nanoparticles coated on the biotin-functionalized PPR-GSC could be determined by the FE-SEM. Average surface coverage rates of Au nanoparticles being activated and without being activated by longitudinal acoustic waves were respectively 18.33% and 18.48%, which were obtained based on calculation with reference to FIGS. 9 and 10. These results suggest that the Au nanoparticles on PPR-GSC are stable under longitudinal acoustic wave action.

Example 9

The instant example demonstrates the removal efficiency of non-specifically bound BSA by longitudinal acoustic waves.

Figure 11:
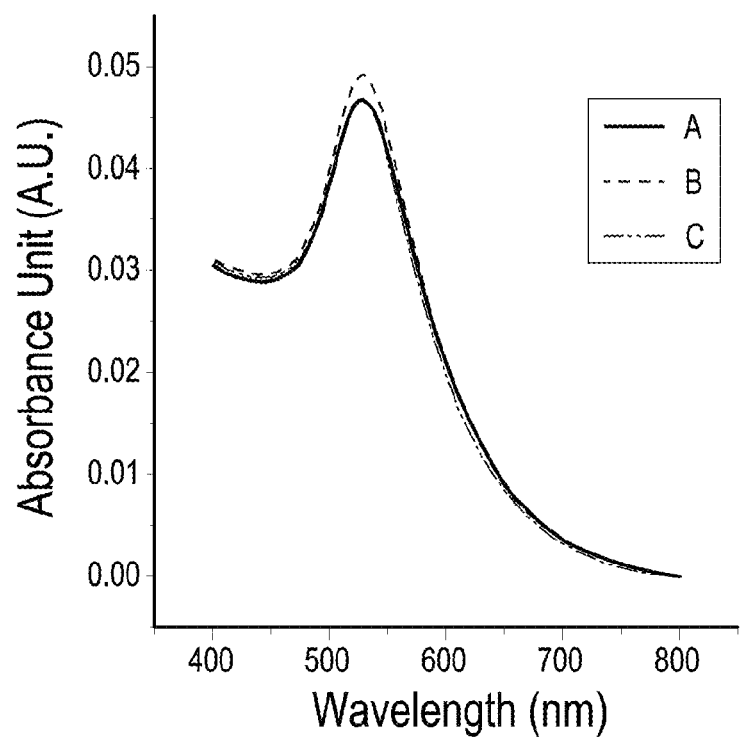
FIG. 11 is a line chart of absorbance spectra of the Au nanoparticles bound with no bovine serum albumin (BSA), bound with BSA and bound with BSA while being activated by longitudinal acoustic waves.

With reference to FIG. 11, the absorbance of Au nanoparticles is represented in FIG. 11 as line A and the absorbance of Au nanoparticles non-specifically bound with BSA is represented in the same FIG. 11 as line B. Comparison of both is directed to an increase in absorbance of Au nanoparticles non-specifically bound with BSA. When Au nanoparticles are activated with longitudinal acoustic waves, as shown as line C in FIG. 11, the absorbance thereof drops to a level roughly the same as the absorbance of the Au nanoparticles bounded with no BSA as line A in FIG. 11.

The above conclusion was obtained with a process comprising the following steps:

1) The biotin-functionalized PPR-GSC was immersed in a $1\times10^{-5}$ g/mL BSA solution for 2 hours.

2) The piezoelectric transducer was driven by a driving voltage of 50 $V_{rms}$ to generate longitudinal acoustic waves whose frequencies linearly swept from 100 kHz to 1 MHz within 10 seconds and then swept back from 1 MHz to 100 kHz within 10 seconds. The foregoing frequency-sweeping operation was defined as a cycle of longitudinal acoustic wave operation. Multiple cycles of the operation may be performed to generate longitudinal acoustic waves. In the instant example, 9 cycles of the foregoing operation were repeated for 3 minutes.

Figure 12:
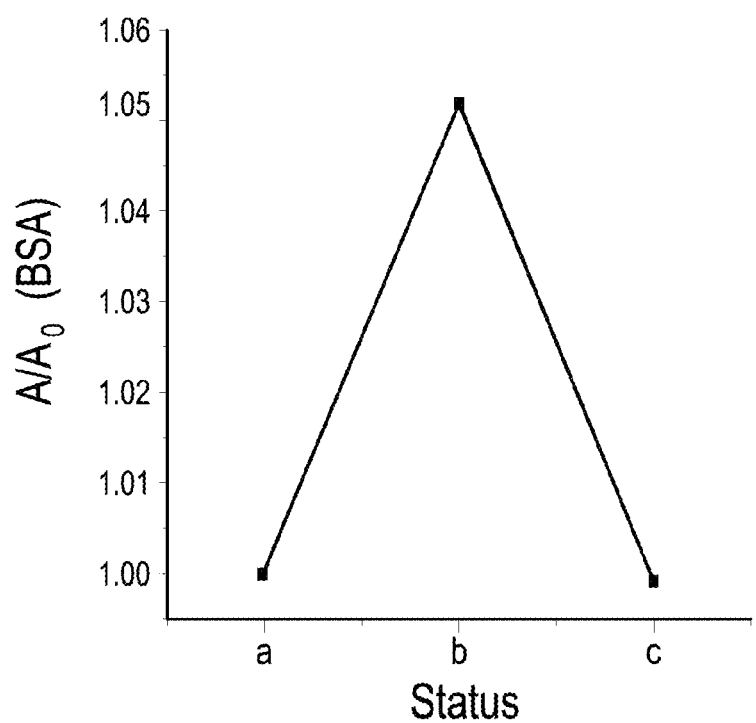
FIG. 12 is a linearized line chart of the Au nanoparticles in FIG. 11 normalized with redefined $A/A_0$ ratio.

The aforementioned process effectively removed non-specifically bound BSA, and allowed the absorbance spectrum of the Au nanoparticles to be reduced back to the level of the spectrum of the original Au nanoparticles prior to the process. With reference to FIG. 11, the results of the aforementioned process were then quantitatively analyzed and normalized. The peak absorbance value of biotin-functionalized PPR-GSC was defined as base value $A_0$. On the other hand, the peak absorbance value of Au nanoparticles of other statuses was defined as A. With reference to FIG. 12, initially without BSA treatment the $A/A_0$ ratio was 1. When PPR-GSC was treated and non-specifically bound with BSA, the $A/A_0$ ratio was 1.05. Being activated with longitudinal acoustic waves, the $A/A_0$ ratio returned to 1. The observations indicate that the removal efficiency of non-specifically bound BSA by longitudinal acoustic waves is 100.0%, which further indicates that longitudinal acoustic waves are capable of successfully removing BSA non-specifically bound to the PPR-GSC.

Example 11

The instant example demonstrates the removal of specifically and non-specifically bound adsorbates from the biotin-functionalized PPR-GSC, wherein the specifically and non-specifically bound adsorbates are respectively anti-biotin antibodies and anti-fibrinogen antibodies.

As shown in previous examples, the covalently-linked objects including Au nanoparticles and biotin were very stable under longitudinal acoustic wave activation. In the instant example, the frequency swept from 100 kHz to 1 MHz, however, the amplitude of driving voltages was altered.

Figure 13:
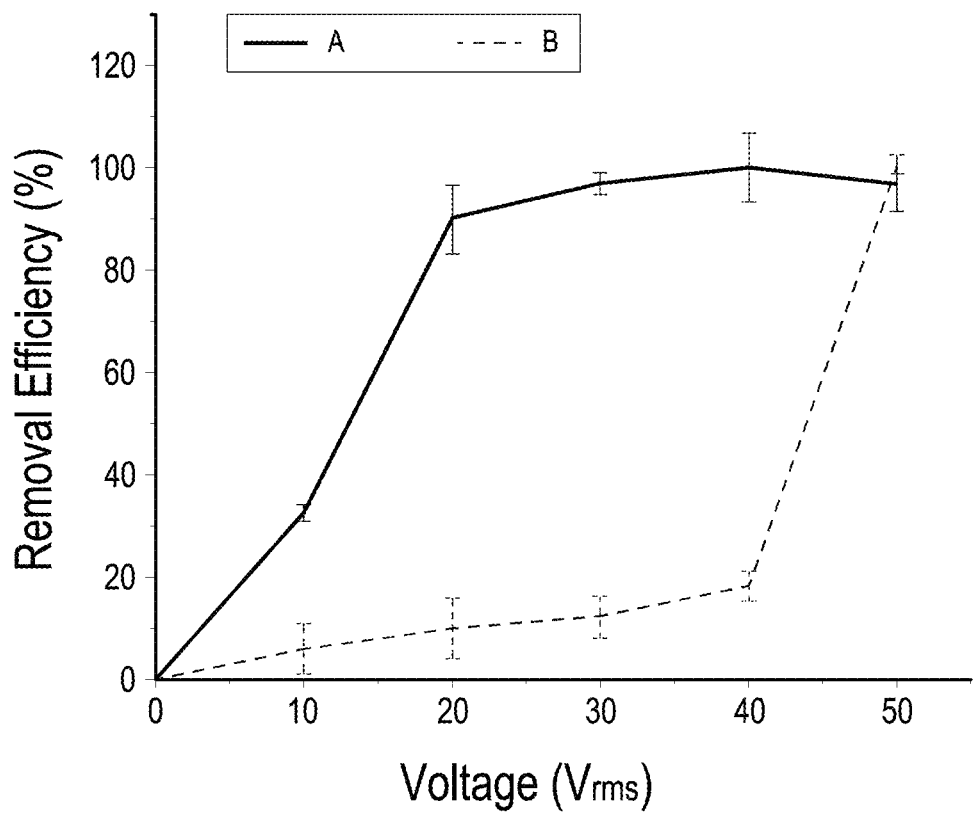
FIG. 13 is a line chart of removal efficiency of non-specifically and specifically bound bioparticles achieved with longitudinal acoustic waves of various voltages.

With reference to FIG. 13, solid line A represents the efficiency of removing non-specifically bound anti-fibrinogen antibodies and dotted line B represents the efficiency of removing anti-biotin antibodies specifically bound with the biotin immobilized on the PPR-GSC. The removal of anti-fibrinogen antibodies and anti-biotin antibodies were performed with different longitudinal acoustic waves generated by the piezoelectric transducer driven by various driving voltages. The removal rate of anti-fibrinogen antibodies was about 30% at 10 $V_{rms}$ and significantly increased to 90% at 20 $V_{rms}$. A driving voltage above 20 $V_{rms}$ was shown to be capable of removing anti-fibrinogen antibodies non-specifically bound to biotin, such that the removal efficiencies using driving voltage above 20 $V_{rms}$ were almost 100%. In contrast, the removal of anti-biotin antibodies specifically bound to biotin required greater acoustic energy to be removed. The removal efficiency of anti-biotin antibodies using a driving voltage under 40 $V_{rms}$ was below 20%. Once the driving voltage applied to the piezoelectric transducer was increased to 50 $V_{rms}$, anti-biotin antibodies could be removed completely.

Example 12

The instant example demonstrates the regeneration of PPR-GSC bound with specific adsorbates.

In the instant example, the regeneration of the PPR-GSC with a target adsorbate bound to a probe, which in the instant example was biotin, was performed with longitudinal acoustic waves of a frequency ranging from 100 kHz to 1 MHz.

Preferably, the longitudinal acoustic waves are of a swept-frequency sweeping from 100 kHz to 1 MHz within a few seconds and sweeping back from 1 MHz to 100 kHz within a few seconds.

Preferably, the driving voltage applied to the piezoelectric transducer is from 0 to 200 $V_{rms}$, so as to remove interfering adsorbates non-specifically bound to the probe or a target adsorbate specifically bound to the probe.

Preferably, the maximum value of the driving voltage is over 50 $V_{rms}$, so as to effectively remove a target adsorbate specifically bound to the probe and thus allow regeneration of the PPR-GSC.

Figure 14:
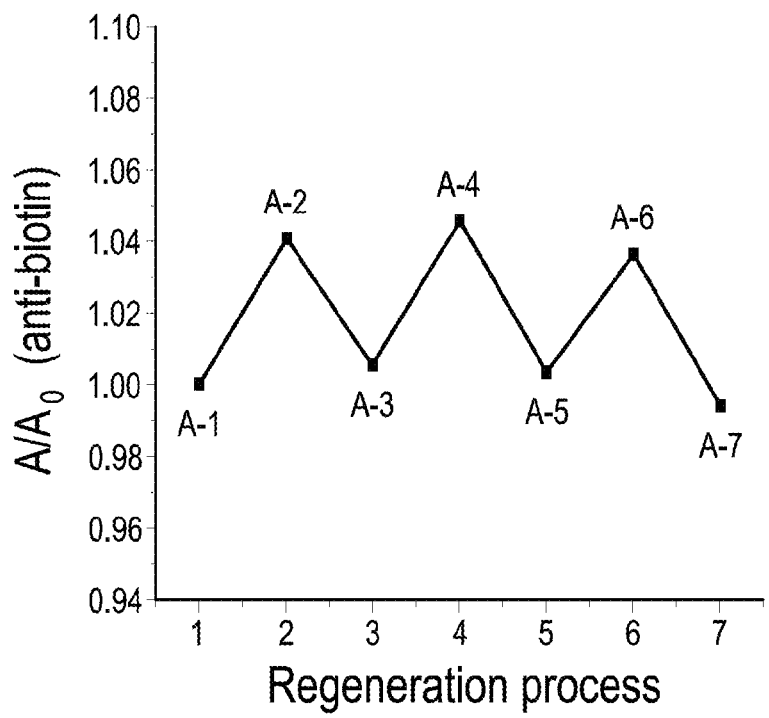
FIG. 14 is a line chart of the regeneration process with longitudinal acoustic waves after binding of anti-biotin antibodies to the biotin immobilized on the surface of biotin-functionalized PPR-GSC.

The regeneration of PPR-GSC with the target adsorbate specifically bound to the probe was measured. With reference to FIG. 14, the uv-visible spectra were, as aforementioned in the previous example, defined to be $A/A_0$ for analysis. When an adsorbate such as anti-biotin antibody or streptavidin is bound to a probe such as biotin, the removal of the adsorbate leads to increase or decrease in absorbance. The result of the measuring was similar to the result disclosed in the aforementioned example. Longitudinal acoustic waves were applied multiple times to the biotin-functionalized PPR-GSC bound with anti-biotin antibodies. The first point A-1 represents the $A/A_0$ ratio of the biotin-functionalized PPR-GSC and the value of the ratio was 1. The PPR-GSC was then immersed in a $1\times10^{-5}$ g/mL anti-biotin antibody to obtain a processed PPR-GSC. The $A/A_0$ ratio of the processed PPR-GSC, being 1.04, is presented in FIG. 14 as point A-2. The PPR-GSC was then further treated with longitudinal acoustic waves to obtain a treated PPR-GSC, whose $A/A_0$ ratio is presented as point A-3 in FIG. 14 and the value thereof was 1.005. As so far demonstrated in the instant example, it is apparent that the PPR-GSC, being treated with longitudinal acoustic waves, was restored to its original state without being bound with anti-biotin antibodies.

Furthermore, in order to demonstrate that longitudinal acoustic waves are capable of repetitively regenerating the PPR-GSC, the foregoing processes for obtaining points A-1 to A-3 were repeated to obtain points A-4 to A-7. It was observed that the $A/A_0$ ratios of points A-5 and A-7, corresponding to the states of the PPR-GSC being treated with longitudinal acoustic waves after being processed with anti-biotin antibodies, returned to the level of the $A/A_0$ ratio of point A-1 corresponding to the original state of the PPR-GSC. The $A/A_0$ ratios of points A-4 and A-6 increased to the level of the $A/A_0$ ratio of point A-2 corresponding to the state of the PPR-GSC processed with anti-biotin antibodies, which demonstrated that the biotin of the regenerated PPR-GSC was capable of binding anti-biotin antibodies.

The foregoing examples have demonstrated that the covalently-linked Au nanoparticles and biotin on the PPR-GSC were stable and functional even after having been regenerated by longitudinal acoustic waves for at least three times.

Example 12

The instant example demonstrates the regeneration of PPR-GSC bound with specific target adsorbates, with a similar process as the previous example except that streptavidin was used in place of anti-biotin antibodies.

Figure 15:
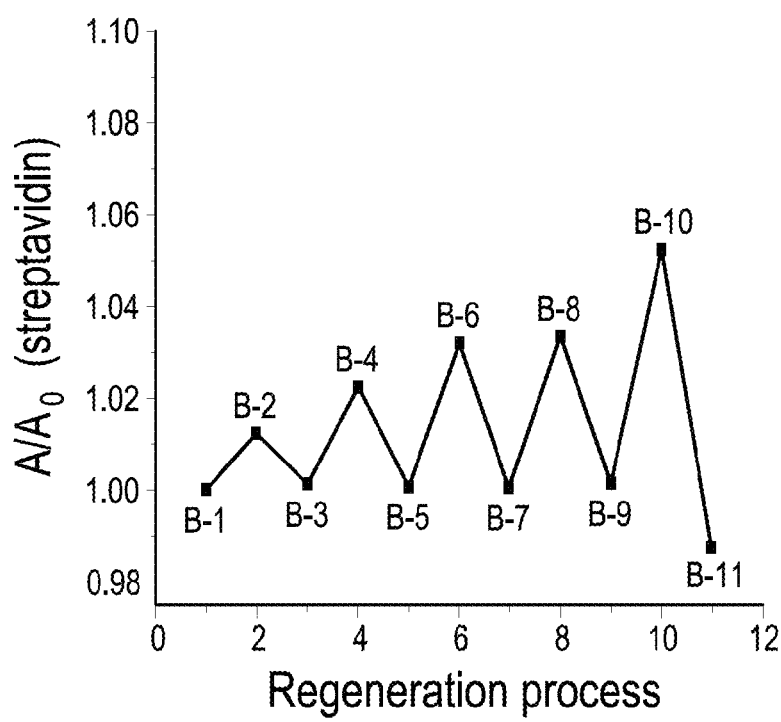
FIG. 15 is a line chart of the regeneration process with longitudinal acoustic waves after binding of streptavidin to the biotin immobilized on the surface of biotin-functionalized PPR-GSC.

With reference to FIG. 15, the biotin-functionalized PPR-GSC was specifically bound with streptavidin and regenerated by longitudinal acoustic waves, as described in the previous example, to sequentially generate points B-1 to B-11, wherein B-1 corresponds to the $A/A_0$ ratio of the PPR-GSC without being processed with streptavidin, while the $A/A_0$ ratios of points B-3, B-5, B-7, B-9 and B-11 correspond to the states of the PPR-GSC processed respectively with streptavidin solutions of concentrations of $2.0 \times 10^{-6}$ g/mL, $5.0 \times 10^{-6}$ g/mL, $1.0 \times 10^{-5}$ g/mL and $5.0 \times 10^{-5}$ g/mL.

Figure 16:
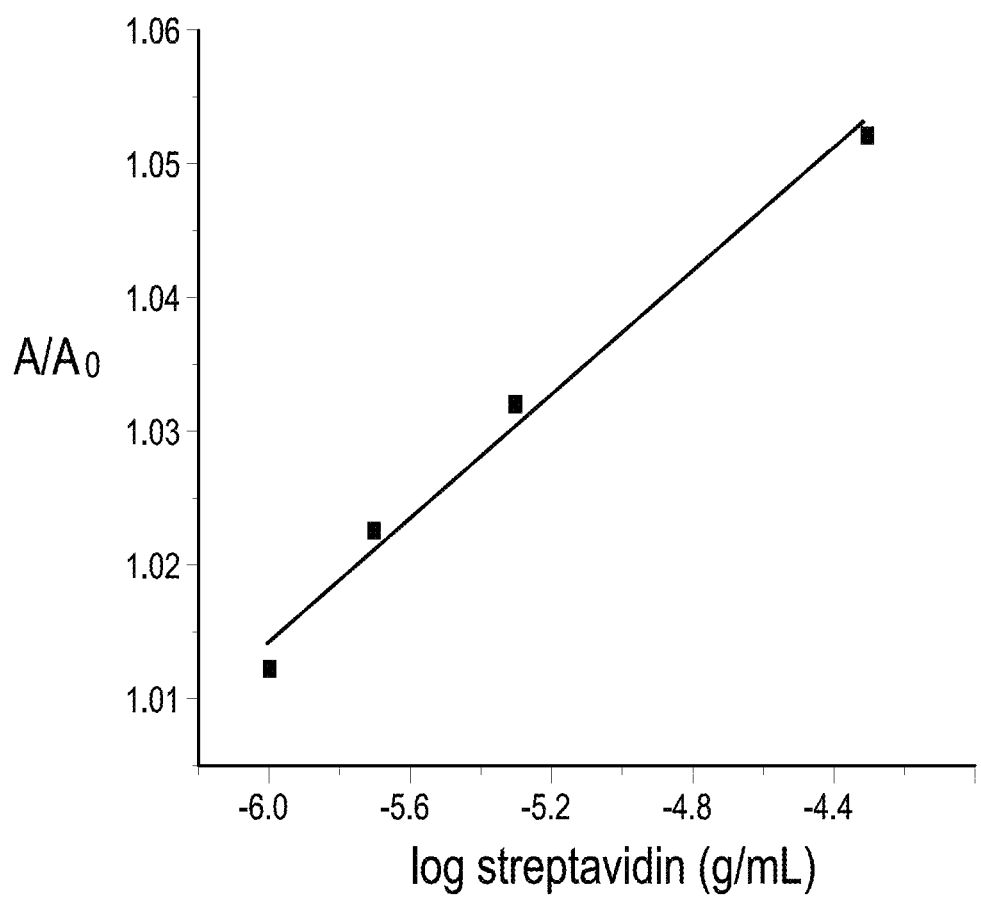
FIG. 16 is a linearized line chart of $A/A_0$ ratio of the biotin immobilized on the surface of biotin-functionalized PPR-GSC under various concentrations of streptavidin in logarithmic scale.

As shown in FIG. 15, it is apparent that even being processed with streptavidin solutions of various concentrations, longitudinal acoustic waves successfully regenerated the biotin-functionalized PPR-GSC in its original state having an $A/A_0$ ratio of 1. In the instant example, it was demonstrated that the biotin-functionalized PPR-GSC could be regenerated at least 5 times. With further reference to FIG. 16, the $A/A_0$ ratios of points B-2, B-4, B-6 and B-8 demonstrate a logarithmic tendency versus streptavidin concentrations.

The method in accordance with the present invention may be operated with an operation system that generates longitudinal acoustic waves to remove, without direct contact, adsorbates bound to the surface of the biochemical sensor chip, that is, the PPR-GSC, as demonstrated in the instant example. The temperature raised to 36° C. does not disable probes and the longitudinal acoustic waves are capable of regenerating the biochemical sensor chip for repetitive use by removing target adsorbates specifically bound to the probes, and are also capable of raising sensitivity, as well as lowering detection limit, by removing interfering adsorbates non-specifically bound to the probes. It was demonstrated that the biochemical sensor chip may be regenerated for at least 5 times, which indicates the present invention to be economical and suitable for commercial applications.

What is claimed is:

1. A method for processing a sensor chip comprising:
providing an acoustic wave operation system and a biochemical sensor chip, wherein the acoustic wave operation system comprises a piezoelectric transducer generating at least one cycle of longitudinal acoustic waves by a driving voltage and wherein a probe is immobilized on a surface of the biochemical sensor chip;
arranging the piezoelectric transducer at a distance from the biochemical sensor chip and filling therebetween with a medium for transmitting longitudinal acoustic waves; and
applying longitudinal acoustic waves to the biochemical sensor chip to remove an adsorbate bound to the probe.

2. The method as claimed in claim 1, wherein the frequency of the longitudinal acoustic waves ranges from 100 kHz to 1 MHz.

3. The method as claimed in claim 1, wherein a cycle of longitudinal acoustic waves comprises longitudinal acoustic waves of a swept-frequency sweeping from 100 kHz to 1 MHz and then back to 100 kHz in a period of time.

4. The method as claimed in claim 3, wherein the piezoelectric transducer applies multiple cycles of longitudinal acoustic waves to the biochemical sensor chip.

5. The method as claimed in claim 1, wherein the biochemical sensor chip further comprises a noble metal nanoparticle layer formed on the surface of the biochemical sensor chip and the probe is attached to the noble metal nanoparticle layer.

6. The method as claimed in claim 1, wherein the distance between the piezoelectric transducer and the biochemical sensor chip ranges from 0.02 mm to 2 mm.

7. The method as claimed in claim 1, wherein the distance between the piezoelectric transducer and the biochemical sensor chip is 0.2 mm.

8. The method as claimed in claim 1, wherein the driving voltage applied to the piezoelectric transducer ranges from 0 $V_{rms}$ to 200 $V_{rms}$ for removing interfering adsorbates non-specifically bound to the probe or a target adsorbate specifically bound to the probe.

9. The method as claimed in claim 1, wherein the driving voltage applied to the piezoelectric transducer is larger than 10 $V_{rms}$ for removing interfering adsorbates non-specifically bound to the probe.

10. The method as claimed in claim 1, wherein the driving voltage applied to the piezoelectric transducer is larger than 10 $V_{rms}$ for removing a target adsorbate bound to the probe.

* * * * *